(12) United States Patent
Mascal

(10) Patent No.: US 7,723,322 B2
(45) Date of Patent: May 25, 2010

(54) FLUORIDE CARRIER FOR POSITRON EMISSION TOMOGRAPHY

(75) Inventor: Mark Mascal, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 165 days.

(21) Appl. No.: 11/693,079

(22) Filed: Mar. 29, 2007

(65) Prior Publication Data
US 2007/0232521 A1    Oct. 4, 2007

Related U.S. Application Data

(60) Provisional application No. 60/787,812, filed on Mar. 31, 2006.

(51) Int. Cl.
*A01N 43/00* (2006.01)
*A61K 31/33* (2006.01)
*C07D 487/00* (2006.01)

(52) U.S. Cl. ........................ 514/183; 540/471

(58) Field of Classification Search ........................ None
See application file for complete search history.

(56) References Cited

OTHER PUBLICATIONS

Daintith, A Dictionary of Chemistry, 1996, p. 407.*
Bing-guang et al. Chemical Communications, 2001, 2652-53.*
Mascal, M. Angewandte Chemie International Edition, 2006, 45, 2890-93.*
Vippagunta et al. Advanced Drug Delivery Reviews, 2001, 48, 3-26.*
Bates, Gareth and Philip A. Gale; "An introduction to anion receptors based on organic frameworks," 2008, *Struct. Bond*, vol. 129, pp. 1-44. Review.
Gale, P. et al.; "Anion receptors based on organic frameworks: highlights from 2005 and 2006," 2008, *Chem. Soc. Rev.*, vol. 37, pp. 151-190. Review.
Hay, Benjamin P. and Vyacheslav S. Bryantsev; "Anion-arene adducts: C-H hydrogen bonding, anion-π interaction, and carbon bonding motifs," 2008, *Chem. Commun.*, pp. 2417-2428.

Mooibroek, T., et al.; "What's new in the realm of anion-π binding interactions? Putting the anion-π interaction in perspective," 2008, *Cyrst. Growth Des.*, vol. 8, pp. 1082-1093.
Schottel, B., et al.; "Anion-π interactions," 2008, *Chem. Soc. Rev.*, vol. 37, pp. 68-83.
Ting, R., et al.; "Arylfluroborates and alkylfluorosilicates as potential PET imaging agents: High-yielding aqueous biomolecular $^{18}$F-labeling," 2005, *J. Am. Chem. Soc.*, vol. 127, pp. 13094-13095.
Yoon, J., et al.; "Imidazolium receptors for the recognition of anions," 2006, *Chem. Soc. Rev.*, vol. 35, pp. 355-360.
Zuo, C-S, et al.; "Oxa-bicyclocalixarenes: A new cage for anions via C-H ••• anion hydrogen bonds and anion ••• π interactions," 2007, *Org. Lett.* vol. 9, pp. 4219-4222.

* cited by examiner

*Primary Examiner*—James O Wilson
*Assistant Examiner*—Noble Jarrell
(74) *Attorney, Agent, or Firm*—Townsend and Townsend and Crew LLP

(57) ABSTRACT

The present invention provides a compound of the formula

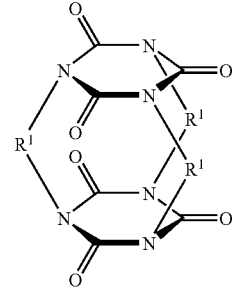

wherein $R^1$ is an ammonium bridge. The compounds of the present invention can be linked to a biological molecule that targets a specific type of cell. The compounds of the present invention can trap isotopic fluorine so that when the biological molecule accumulates in the desired type of cell, the isotopic fluorine is imaged by positron emission tomography (PET).

9 Claims, 1 Drawing Sheet

FLUORIDE CARRIER FOR POSITRON EMISSION TOMOGRAPHY

CROSS-REFERENCES TO RELATED APPLICATIONS

This application claims the benefit of U.S. Provisional Application No. 60/787,812, filed Mar. 31, 2006.

STATEMENT AS TO RIGHTS TO INVENTIONS MADE UNDER FEDERALLY SPONSORED RESEARCH AND DEVELOPMENT

[Not Applicable]

BACKGROUND OF THE INVENTION

Positron emission tomography (PET) is a non-invasive diagnostic technique of rapidly growing importance in the field of oncology. Since molecular events associated with cancer are directly observed using this method, custom tracers allow more specific identification of malignancies than simple anatomy-based imaging. An additional advantage of PET is an order of magnitude greater sensitivity than the single photon computerized tomography method used with gamma emitters (e.g. 99 mTc labeled probes).

The ideal tracer probe for imaging cancer would have the following characteristics: 1) it would accumulate specifically in targeted cells, 2) it would clear rapidly from blood and surrounding tissues not associated with the tumor, 3) the attachment of the radionuclide would not substantially diminish the affinity of the tracer molecule for its target, 4) the radionuclide would not be easily dissociated from the tracer molecule in vivo, 5) given the short half-life of positron emitting isotopes, the protocol for introducing the radionuclide into the probe should be as quick and efficient as possible.

The most commonly used isotope for PET is $^{18}$F, which is produced by proton bombardment of $^{18}$OH$_2$ and has a comparatively long half life of 110 minutes. In the majority of clinical PET scans, the tracer probe is 2-$^{18}$F-2-deoxy-D-glucose (FDG) ("Positron Emission Tomography with [$^{18}$F]-FDG in Oncology." J. N. Talbot, Y. Petegnief, K. Kerrou, F. Montravers, D. Grahek, N. Younsi, Nuclear Instruments and Methods in Physics Research A 2003, 504, 129), which is recognized by cells as glucose and taken up, but can not be utilized. FDG thus accumulates in the cells and a metabolic image of the tumor is obtained.

There are however a number of disadvantages to the use of FDG. First, it gives no direct indication of the neoplastic character of the lesion. Second, well-differentiated and slow-growing tumors are often not detected. Third, although it is highly useful for the management of certain cancers (e.g. lung, melanoma), it is less effective for others, e.g. those of the brain, where background glucose uptake is also rapid.

A potential answer to these issues can be found in the labeling of ligands which are specifically recognized by particular cancer cells. Since these can be cell-surface receptor proteins or even macromolecules (e.g. antibodies, diabodies, minibodies), there is substantially more leeway for the attachment of the label, and indeed macrocyclic $^{64}$Cu and $^{68}$Ga complexes have been developed in this context which would be much too large for the labeling of glucose ("Targeting Peptides and Positron Emission Tomography." H. Lundqvist, V. Tolmachev, Biopolymers 2002, 66, 381). An advantage of using metal-macrocycle chelation is that the synthetic work required (i.e. attachment of the label to the molecular probe) can be done before the arrival of the radionuclide, which is simply complexed by the chelator-tracer conjugate and is ready for use. Unfortunately, $^{64}$Cu and $^{68}$Ga are far less readily available than $^{18}$F, which limits their widespread application in both research and therapy.

The practical scope for recognition and binding of anions is considerably narrower than that for metal cations ("Anion Recognition and Sensing: The State of the Art and Future Perspectives." P. D. Beer, P. A. Gale, Angew. Chem. Int. Ed. 2001, 40, 486). One reason for this is because concentrations of negative potential are more accessible and manageable on the molecular scale than concentrations of positive potential. Thus while examples of electron wells abound in the form of easily manipulable heteroatom arrays, localized electron deficits involve Lewis acidic sites which are less conveniently integrated into receptor design than the common nonmetals, and are generally incompatible with the only other vectorial noncovalent interaction relevant to anions, i.e., hydrogen bonding.

Aromatic rings are intuitively sources of electron density, and much work has been done on their interaction with cations. However, heterocyclic and perfluorinated rings show a minimum in electrostatic potential at their centroids, thereby making a favorable interaction between such rings and anions possible. Using high level quantum mechanical modeling (MP2/6-31G*), we found an interaction on the order of 10 kcal mol-1 for s-triazine complexes with fluoride and chloride as the representative anions ("Anion-Aromatic Bonding: A Case for Anion Recognition by π-Acidic Rings." M. Mascal, A. Armstrong, M. D. Bartberger, J. Am. Chem. Soc. 2002, 124, 6274). The optimized triazine centroid . . . anion distances for fluoride and chloride were about 2.6 and 3.2 Å, respectively.

Since present techniques for labeling peptides with $^{18}$F are laborious and not yet of clinical value, the best case scenario would be a system which achieved customized imaging using cell-line specific peptides, and incorporated an $^{18}$F$^-$ complexing agent to disinvolve chemical transformations from the labeling process. Surprisingly, the present invention meets this and other needs.

BRIEF SUMMARY OF THE INVENTION

In one embodiment, the present invention provides a compound having the formula:

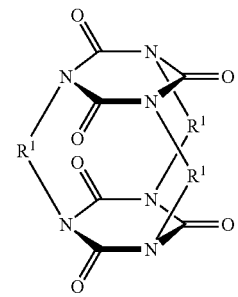

wherein R$^1$ is

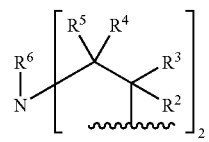

R$^2$ and R$^3$ are each hydrogen. R$^4$ and R$^5$ are each hydrogen, or combined to form =O. Each R$^6$ is independently a member selected from the group consisting of H, optionally substituted C$_1$-C$_{10}$ alkyl, C$_1$-C$_6$ alkyl-CO$_2$H, C$_1$-C$_6$ alkyl- CONHR$^7$, optionally substituted $C_5$-$C_{10}$ cycloalkyl, optionally substituted $C_6$-$C_{12}$ aryl, optionally substituted $C_5$-$C_{12}$ heteroaryl and L-B, wherein L is a linker and B is a biological molecule selected from the group consisting of a peptide, a protein and a saccharide. Each R$^7$ is independently a member selected from the group consisting of H and $C_1$-$C_6$ alkyl. Alternatively, R$^4$, R$^5$ and R$^6$ are combined to form a 5-6 membered heteroaryl ring having from 1-3 heteroatoms each independently selected from the group consisting of N, O and S, optionally substituted with 1-3 R$^8$. Alternatively, R$^2$, R$^3$, R$^4$, R$^5$ and R$^6$ are combined to form a 11-14 membered heteroaryl ring having from 1-3 heteroatoms each independently selected from the group consisting of N, O and S, optionally substituted with 1-3 R$^8$. Each R$^8$ is independently a member selected from the group consisting of H, optionally substituted $C_1$-$C_6$ alkyl, optionally substituted $C_5$-$C_{10}$ cycloalkyl, optionally substituted $C_6$-$C_{12}$ aryl, optionally substituted $C_5$-$C_{12}$ heteroaryl and L-B, wherein L is a linker and B is a biological molecule selected from the group consisting of a peptide, a protein and a saccharide. The present invention also provides the pharmaceutically acceptable salts, hydrates and isomers of the compounds.

In another embodiment, R$^1$ is a member selected from the group consisting of:

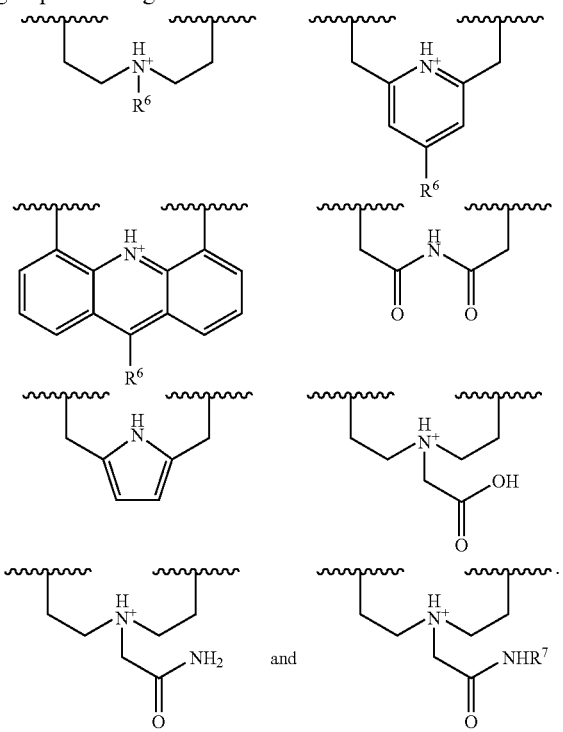

In still another embodiment, R$^1$ is

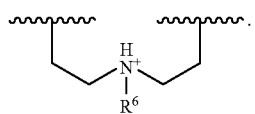

In yet still another embodiment, R$^2$, R$^3$, R$^4$ and R$^5$ are each H.

In some embodiments, R$^6$ is a member selected from the group consisting of $C_1$-$C_{10}$ alkyl and $C_6$-$C_{12}$ aryl. In other embodiments, R$^6$ is a member selected from the group consisting of hexyl and benzyl.

In some other embodiments, R$^1$ is

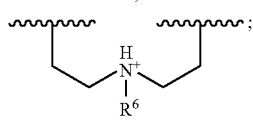

and R$^6$ is hexyl. In still other embodiments, R$^1$ is

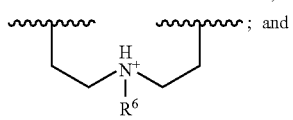

R$^6$ is benzyl.

In yet another embodiment, L-B is a member selected from the group consisting of:

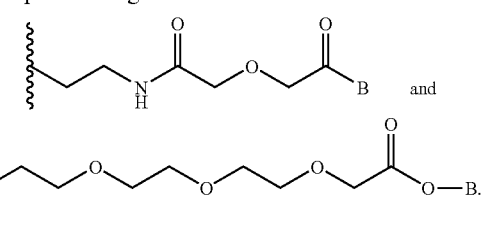

In still yet another embodiment, B is a peptide.

In other embodiments, the present invention provides a compound having the formula:

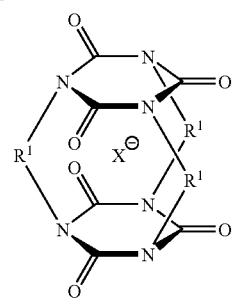

wherein X is $^{18}$F.

In a second embodiment, the present invention provides a composition comprising a compound as described above and a pharmaceutical excipient. In another embodiment, the compound of the composition has the formula:

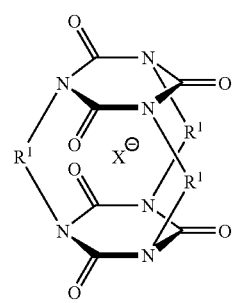

wherein X is $^{18}$F. In still another embodiment, the composition further comprises a biological molecule selected from the group consisting of a peptide, a protein and a saccharide.

In a third embodiment, the present invention provides a method for imaging cancer cells. The first step of the method involves administering to a patient in need thereof a compound as described above in combination with $^{18}F^-$. The second step involves imaging where the $^{18}F^-$ accumulates. In some embodiments, the imaging is accomplished via positron emission tomography.

DETAILED DESCRIPTION OF THE INVENTION

I. Definitions

Figure 1:
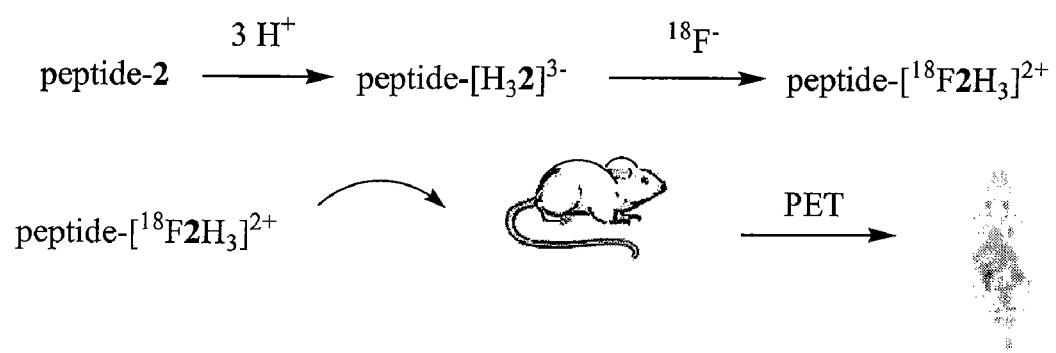
FIG. 1. An outline for the clinical implementation of this invention is provided. Compound 14 is conjugated to the appropriate tracer protein using standard peptide chemistry and then "armed" by tris-protonation to activate it towards fluoride. The conjugate is then added to a neutral solution of accelerator-produced $^{18}F^-$ and the complex is ready for injection into the subject and imaging by PET.

As used herein, the term "alkyl" refers to a straight or branched, saturated, aliphatic radical having the number of carbon atoms indicated. For example, $C_{1-4}$alkyl includes methyl, ethyl, propyl, butyl, isopropyl, isobutyl or tert-butyl. One of skill in the art will appreciate that other alkyls groups are useful in the present invention.

Substituents for the alkyl group (including those groups often referred to as alkylene, alkenyl, alkynyl, cycloalkyl, heterocycloalkyl, cycloalkenyl) can be a variety of groups selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O) R', —S(O)$_2$R', —S(O)$_2$NR'R", —CN and —NO$_2$ in a number ranging from zero to (2m'+1), where m' is the total number of carbon atoms in such radical. R', R" and R''' each independently refer to hydrogen, unsubstituted ($C_1$-$C_8$)alkyl and heteroalkyl, unsubstituted aryl, unsubstituted alkyl, alkoxy or thioalkoxy groups, or aryl-($C_1$-$C_4$)alkyl groups.

As used herein, the term "aryl" refers to a monocyclic or fused bicyclic or tricyclic aromatic ring assembly containing six to sixteen ring carbon atoms. For example, aryl may be phenyl, benzyl or naphthyl, preferably phenyl. Aryl groups can be substituted by one, two or three radicals selected from alkyl, alkoxy, aryl, hydroxy, halogen, cyano, amino, aminoalkyl, trifluoromethyl, alkylenedioxy and oxy-$C_2$-$C_3$-alkylene; all of which are optionally further substituted; or 1- or 2-naphthyl; or 1- or 2-phenanthrenyl. Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

As used herein, the term "cycloalkyl" refers to a saturated or partially unsaturated, monocyclic, fused bicyclic or bridged polycyclic ring assembly containing from 3 to 10 ring atoms. For example, $C_{3-10}$ cycloalkyl includes cyclopropyl, cyclobutyl, cyclopentyl, cyclohexyl, etc. "Heterocycloalkyl" means cycloalkyl having one or more of the ring carbons indicated replaced by a moiety selected from —O—, —N=, —NR—, —S—, —S(O)— or —S(O)$_2$—, wherein R is hydrogen, $C_{1-4}$alkyl or a nitrogen protecting group. For example, $C_{3-8}$heterocycloalkyl-$C_{0-4}$alkyl as used in this application to describe compounds of the invention includes morpholino, morpholino-methyl, morpholino-ethyl, pyrrolidinyl, piperazinyl, piperidinyl, piperidinylone, 1,4-dioxa-8-aza-spiro[4.5]dec-8-yl, etc.

As used herein, the term "heteroaryl" refers to a monocyclic or fused bicyclic or tricyclic aromatic ring assembly containing 5 to 16 ring atoms, where from 1 to 4 of the ring atoms are a heteroatom each selected from the group consisting of N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl. Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O) R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O) R', —S(O)$_2$R', —S(O)$_2$NR'R", —N$_3$, —CH(Ph)$_2$, perfluoro ($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "linker" refers to a chemical moiety that links the compound of the present invention to a biological material that targets a specific type of cell, such as a cancer cell, other type of diseased cell, or a normal cell type. Linkers useful in the present invention can be up to 30 atoms in length. Preferably, the linkers are 5-15 atoms in length. The types of bonds used to link the linker to the compound and biological molecule of the present invention include, but are not limited to, amides, amines, esters, carbamates, ureas, thioethers, thiocarbamates, thiocarbonate and thioureas. One of skill in the art will appreciate that other types of bonds are useful in the present invention.

As used herein, the term "biological molecule" refers to a peptide, protein, saccharide, polysaccharide, nucleotide, antibody or any other compound that can target a specific type of cell, such as cancer cells or other disease-type cells. One of skill in the art will appreciate that other types of biological molecules are useful in the present invention.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference. A preferred salt of the present invention is a $F^-(NR_4^+)_3$ salt.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "hydrate" refers to a compound that is complexed to at least one water molecule. The compounds of the present invention can be complexed with from 1 to 10 water molecules.

As used herein, the term "isomer" refers to compounds of the present invention that possess asymmetric carbon atoms (optical centers) or double bonds; the racemates, diastereomers and geometric isomers are all intended to be encompassed within the scope of the present invention.

As used herein, the term "$^{18}F$" refers to isotope 18 of the element fluorine. Naturally occurring fluorine has nine protons and 10 neutrons. Fluorine-18 ($^{18}F$) has only nine neutrons and nine protons. The half-life of fluorine-18 is approximately 110 minutes. Fluorine-18 can be produced from $^{18}OH_2$ in a cyclotron, or by other methods known to one of skill in the art.

As used herein, the term "pharmaceutical excipient" refers to a substance that aids the administration of an active agent to and absorption by a subject. Pharmaceutical excipients useful in the present invention include, but are not limited to, binders, fillers, disintegrants, solvents, lubricants, coatings, sweeteners, flavors and colors. One of skill in the art will recognize that other pharmaceutical excipients are useful in the present invention.

As used herein, the term "imaging" refers to using a device outside of the subject to determine the location of an imaging agent, such as a compound of the present invention. Examples of imaging tools include, but are not limited to, positron emission tomography (PET), magnetic resonance imaging (MRI), ultrasound, single photon emission computed tomography (SPECT) and x-ray computed tomography (CT). The positron emission tomography detects radiation from the emission of positrons by an imaging agent.

II. Compounds

The invention involves specific derivatives of 15,20,25-triaza[5.5.5]-1,3,5-cyclophane, which have been determined to act as hosts for the fluoride anion. Because the compounds can bind fluoride so effectively, they form the basis of a novel radionuclide labeling method for positron emission tomography, which utilizes almost exclusively the radioisotope $^{18}F$.

The compounds of the present invention have the formula

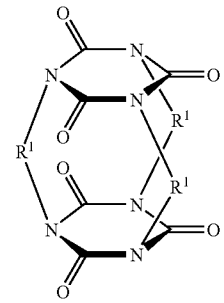

wherein $R^1$ is

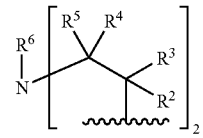

wherein $R^2$ and $R^3$ are each hydrogen. R4 and $R^5$ are each hydrogen, or combined to form =O. Each $R^6$ is independently a member selected from the group consisting of H, optionally substituted $C_1$-$C_{10}$ alkyl, $C_1$-$C_6$ alkyl-$CO_2H$, $C_1$-$C_6$ alkyl-$CONHR^7$, optionally substituted $C_5$-$C_{10}$ cycloalkyl, optionally substituted $C_6$-$C_{12}$ aryl, optionally substituted $C_5$-$C_{12}$ heteroaryl and L-B, wherein L is a linker and B is a biological molecule selected from the group consisting of a peptide, a protein and a saccharide. Each $R^7$ is independently a member selected from the group consisting of H and $C_1$-$C_6$ alkyl. Alternatively, $R^4$, $R^5$ and $R^6$ are combined to form a 5-6 membered heteroaryl ring having from 1-3 heteroatoms each independently selected from the group consisting of N, O and S, optionally substituted with 1-3 $R^8$. Alternatively, $R^2$, $R^3$, $R^4$, $R^5$ and $R^6$ are combined to form a 11-14 membered heteroaryl ring having from 1-3 heteroatoms each independently selected from the group consisting of N, O and S, optionally substituted with 1-3 $R^8$. Each $R^8$ is independently a member selected from the group consisting of H, optionally substituted $C_1$-$C_6$ alkyl, optionally substituted $C_5$-$C_{10}$ cycloalkyl, optionally substituted $C_6$-$C_{12}$ aryl, optionally substituted $C_5$-$C_{12}$ heteroaryl and L-B, wherein L is a linker and B is a biological molecule selected from the group consisting of a peptide, a protein and a saccharide; and pharmaceutically acceptable salts, hydrates and isomers thereof.

A broad range of possibilities for both the two bridgehead six-membered rings and the three 5-membered amine bridges are possible. The rings include, but are not limited to, cyanuric acid, 1,3,5-triazine, 1,3,5-trifluorobenzene, transition metal eta-6 complexed benzene, 1,3,5-tricyanobenzene, 1,3,5-trinitrobenzene, and 1,3,5-triacylbenzene rings.

The bridges include, but are not limited to, 3-azapent-1,5-yl, 2,6-dimethylenepyridyl, 4,5-acridinyl, 2,4-diketo-3-azapent-1,5-yl, or 1,4-dimethylenepyrrolyl. Any of these may include substituent R groups. The R groups can be up to 20 carbon atoms in length. Preferably, the R groups are 5 to 15 carbons in length. The R substituent can also connect the cyclophane to the biological molecule, in which case the substituent terminates with a functional group, such as amine or carboxylate. Additionally, the 3-azapent-1,5-yl bridge can include substituent R groups in which a hydrogen bonding function (carboxylic acid or amide) is present one carbon removed from the N. Such substituents may act to further stabilize the complexation of fluoride.

Bridges useful in the compounds of the present invention include where $R^1$ is selected from the group consisting of:

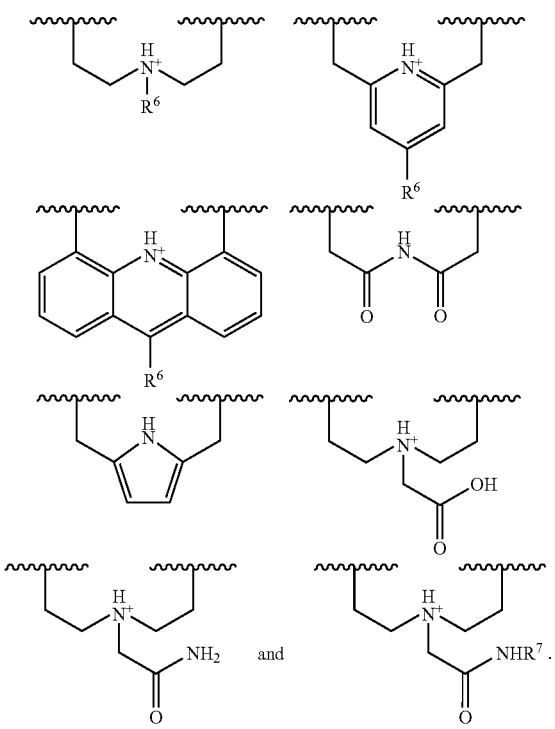

In some instances, $R^1$ is

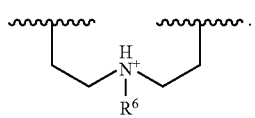

The compounds of the present invention include those where $R^2$, $R^3$, $R^4$ and $R^5$ are each H.

$R^6$ can be $C_1$-$C_{10}$ alkyl or $C_6$-$C_{12}$ aryl, preferably hexyl or benzyl. When $R^1$ is

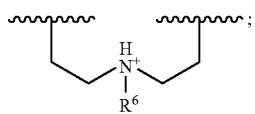

$R^6$ can be hexyl or benzyl.

The linkers of the present invention are chemical moieties that link the compound of the present invention to a biological material of the present invention that targets a specific type of cell. Linkers useful in the present invention can be up to 30 chain atoms in length. Preferably, the linkers are 5-15 chain atoms in length. Two examples of linkers useful in the present invention are those shown below:

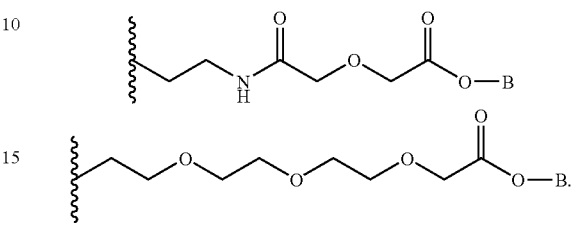

Other linkers useful in the present invention will be recognized by one of skill in the art of positron emission tomography and linking caged compounds to biological molecules.

A variety of methods known to one of skill in the art can be used to attach the linker to a compound of the present invention. The compound of the present invention can have one linker attached via one $R^1$ bridge, or two linkers attached via two $R^1$ bridges, or three linkers attached via three $R^1$ bridges. The $R^1$ bridges may additionally accommodate more than one linker each. The types of bonds used to link the linker to the compound and biological molecule of the present invention include, but are not limited to, amides, amines, esters, carbamates, ureas, thioethers, thiocarbamates, thiocarbonate and thioureas. A preferred biological molecule is a peptide. One of skill in the art will appreciate that other types of bonds are useful in the present invention.

Scheme 1. Attachment of Linker to Compound 1.

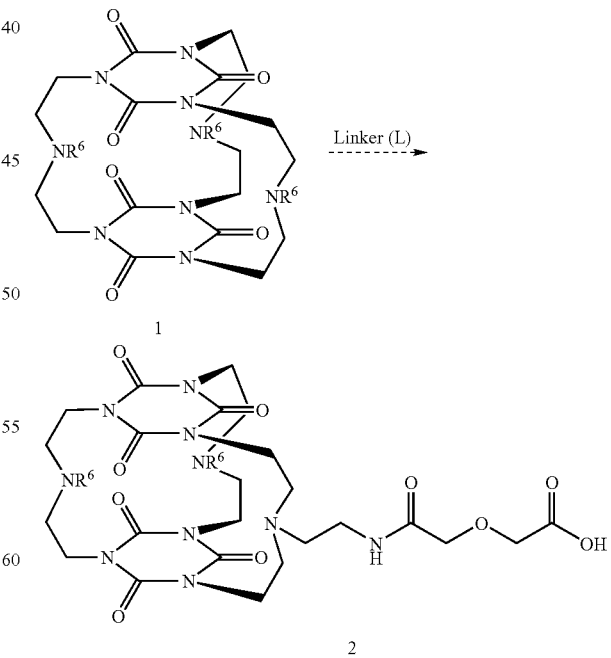

The compounds of the present invention can be linked to any biological molecule or moiety that is capable of targeting a specific type of cell in a subject. The subject can be a mammal such as a horse, dog, cat, rat, mouse, monkey or human. Biological molecules useful in the present invention include, but are not limited to, peptides, proteins, saccharides, polysaccharides, nucleotides and antibodies. Attachment of the biological molecule to a compound of the present invention can be accomplished by a variety of methods known to one of skill in the art, including peptide chemistry known to one of skill in the art. One of skill in the art will appreciate that other biological molecules are useful in the present invention.

III. Compositions

Compositions useful in the present invention include a compound of the present invention and a pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art. Pharmaceutical excipients useful in the present

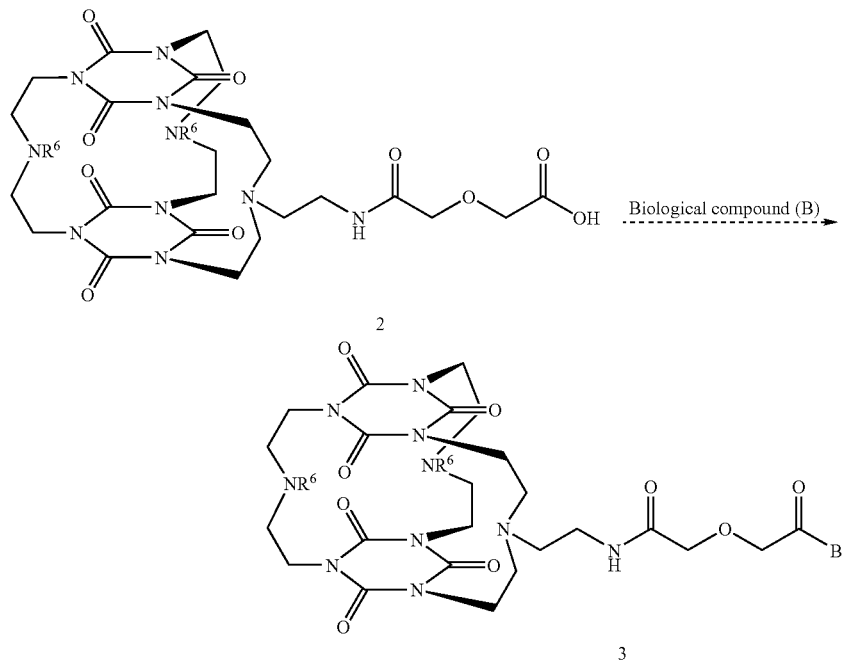

The biological molecules of the present invention are capable of targeting a specific type of cell in a subject. Cells useful in the present invention include, but are not limited to, diseased cells such as cancer, and any type of normal cell. One of skill in the art will appreciate that other types of diseased cells are useful in the present invention.

The compounds of the present invention are preferably in a salt form, such as shown by the following formula:

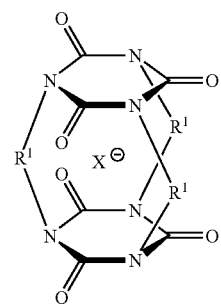

wherein X is $^{18}F$. Other salts of the compounds of the present invention are useful in the present invention.

invention include, but are not limited to, binders, fillers, disintegrants, solvents, lubricants, coatings, sweeteners, flavors and colors.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols. One of skill in the art will appreciate that other pharmaceutically acceptable excipients are useful in the present invention.

IV. Methods

The present invention provides a method for imaging cancer cells comprising the step of administering to a patient in need thereof a compound of the present invention in combination with $^{18}F^-$, and imaging where the $^{18}F^-$ accumulates. The imaging can be accomplished by a variety of methods known to one of skill in the art, including, but not limited to, positron emission tomography (PET), magnetic resonance imaging (MRI), ultrasound, single photon emission computed tomography (SPECT) and x-ray computed tomography (CT). One of skill in the art will appreciate that other imaging techniques are useful in the present invention.

V. EXAMPLES

The compounds of the present invention can be accomplished by two related routes.

Example 1

Preparation of Compound 1: $R^6$=n-hexyl

Scheme 3 starts from the commercially available diethanolamine 4, which was N-alkylated with 1-bromohexane to give 5 and then monosilylated to give 6. Substitution of alcohol 6 for chloride gave 7, which reacted with cyanuric acid in the presence of 1,8-diazabicyclo[5.4.0]undec-7-ene (DBU) to give 8. Desilylation of 8 with tetrabutylammonium fluoride (Bu$_4$NF) gave triol 9, the substitution of which for chloride gave 10. Reaction of 10 with cyanuric acid in the presence of DBU gave the target cyclophane 1 ($R^6$=n-hexyl).

anhydrous MgSO$_4$ and the solvent was evaporated under reduced pressure to give 5 (44.3 g, 78%) as a clear oil: IR (KBr) 3490, 2910 cm$^{-1}$; $^1$H NMR (300 MHz; CDCl$_3$) δ 0.89 (3H, t), 1.28 (6 H, m), 1.46 (2 H, m), 2.53 (2 H, t), 2.66 (4 H, t), 3.01 (2 H, br s), 3.62 (4 H, t); $^{13}$C NMR (75 MHz; CDCl$_3$) δ 13.99, 22.59, 26.83, 26.97, 31.70, 54.74, 56.02, 59.51.

Synthesis of 6. Sodium hydride (95%, 1.66 g, 66 mmol) was added in portions to a stirred solution of 5 (15.37 g, 81.2 mmol) in dry tetrahydrofuran (300 mL) at room temperature under a nitrogen atmosphere, and the resulting suspension was stirred for 30 minutes. Triisopropylsilyl chloride (17.2 mL, 15.5 g, 80.4 mmol) was added dropwise and stirring was continued for 10 hours. The reaction mixture was washed with brine (3×200 mL) and the organic phase was dried over anhydrous MgSO$_4$ and evaporated under reduced pressure. Column chromatography of the residue on silica gel (4:1 n-hexane:EtOAc) gave 6 (12.93 g, 57%) as a clear oil: IR (KBr) 3502, 2928 cm$^{-1}$; $^1$H NMR (300 MHz; CDCl$_3$) δ 0.88 (3 H, t), 1.06 (21 H, m), 1.27 (6 H, m), 1.44 (2 H, m), 2.51 (2 H, t), 2.65 (4 H, m), 3.21 (1 H, br s), 3.52 (2 H, t), 3.73 (2 H,

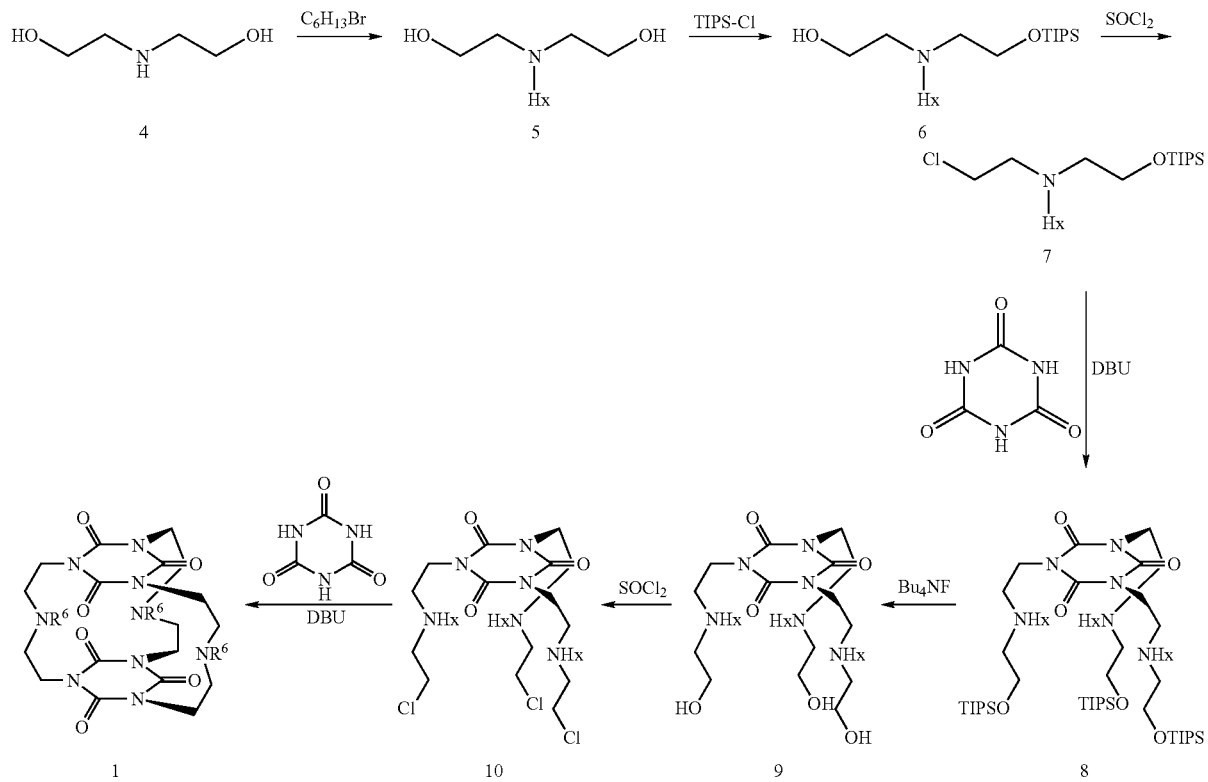

Scheme 3. Preparation of Compound 1 ($R^6$ = n-hexyl).

Synthesis of 5. 1-Bromohexane (42.3 mL, 49.7 g, 0.301 mol) was added to a stirred mixture of diethanolamine 4 (31.5 mL, 34.6 g, 0.329 mol) and Na$_2$CO$_3$ (38.15 g, 0.36 mol) in acetonitrile (1.2 L). The mixture was heated at reflux for 48 hours with stirring under a nitrogen atmosphere. After this time the mixture was cooled to room temperature, filtered, and the solvent was removed under reduced pressure. The residue was dissolved in chloroform (300 mL) and washed with brine (5×150 mL). The organic phase was dried over t); $^{13}$C NMR (75 MHz; CDCl$_3$) δ 12.08, 14.22, 18.14, 22.80, 27.15, 27.54, 31.96, 55.07, 56.22, 56.23, 59.02, 62.10.

Synthesis of 7. Thionyl chloride (3.16 mL, 5.15 g, 43.3 mmol) was added dropwise to a solution of 6 (7.52 g, 21.8 mmol) in dry dichloromethane (150 mL) at room temperature under a nitrogen atmosphere. The mixture was stirred for 16 hours and then poured into saturated aqueous NaHCO$_3$ (600 mL). The mixture was extracted with dichloromethane (3×100 mL), the combined organic extract was dried (MgSO$_4$), and the solvent was evaporated under reduced pressure to give 7 (7.00 g, 88%) as a pale yellow oil: IR (KBr) 2939, 1050, 812 cm$^{-1}$; $^1$H NMR (300 MHz; CDCl$_3$) δ 0.88 (3 H, t), 1.08 (21 H, m), 1.27 (6 H, m), 1.44 (2 H, m), 2.54 (2 H, t), 2.69 (2 H, t), 2.87 (2 H, t), 3.50 (2 H, t), 3.71 (2 H, t); $^{13}$C NMR (75 MHz; CDCl$_3$) δ 12.05, 13.81, 14.20, 17.84, 18.16, 22.79, 27.08, 31.88, 42.18, 55.59, 55.68, 56.85.

Synthesis of 8. Compound 7 (7.00 g, 19.2 mmol) and 1,8-diazabicyclo[5.4.0]undec-7-ene (5.74 mL, 5.84 g, 38.4 mmol) were added to a solution of cyanuric acid (0.790 g, 6.12 mmol) in freshly distilled N,N-dimethylformamide (65 mL). The mixture was heated at 70° C. for 16 hours under a nitrogen atmosphere. The reaction was cooled to room temperature and the solvent was removed under reduced pressure. The crude product was purified by column chromatography on silica gel (0 to 5% MeOH:CH$_2$Cl$_2$) to give 8 (6.17 g, 91%) as a pale yellow oil: IR (KBr) 2943, 2865, 1695 cm$^{-1}$; $^1$H NMR (300 MHz; CDCl$_3$) δ 0.87 (9 H, t), 1.05 (65 H, m), 1.25 (16 H, m), 1.38 (6 H, m), 2.52 (6 H, t), 2.68 (12 H, m), 3.71 (6 H, t), 3.91 (6 H, t); $^{13}$C NMR (75 MHz; CDCl$_3$) δ 11.90, 14.05, 17.99, 22.68, 26.96, 27.58, 31.83, 40.78, 51.82, 55.11, 56.44, 62.22, 148.88.

Synthesis of 9. To a solution of 8 (1.98 g, 1.78 mmol) in tetrahydrofuran (50 mL) was added a solution of tetrabutylammonium fluoride in tetrahydrofuran (1.0 M, 10.5 mL, 10.5 mmol) at 0° C. under a nitrogen atmosphere. After 10 minutes, the reaction mixture was allowed to warm to room temperature and left stirring for 4 hours. Water (100 mL) was added and the aqueous layer was separated and extracted with CH$_2$Cl$_2$ (4×200 mL). The organic phases were combined, dried over MgSO$_4$, and the solvent was evaporated under reduced pressure. The crude product was purified by column chromatography on silica gel (0 to 10% MeOH:CH$_2$Cl$_2$) to give 9 (0.60 g, 52%) as a pale yellow oil: IR (KBr) ν 3302, 2958, 1688 cm$^{-1}$; $^1$H NMR (300 MHz; CDCl$_3$) δ 0.87 (9 H, t), 1.24 (18 H, m), 1.37 (6 H, m), 2.48 (6 H, t), 2.65 (6 H, t), 2.73 (6 H, t), 2.95 (3 H, br s), 3.53 (6 H, t), 3.96 (6 H, t); $^{13}$C NMR (75 MHz; CDCl$_3$) δ 14.04, 22.64, 26.92, 27.12, 31.77, 41.28, 51.35, 54.39, 56.28, 58.90, 149.33.

Synthesis of 10. Thionyl chloride (0.88 ml, 1.44 g, 12.1 mmol) was added dropwise to a solution of 9 (1.30 g, 2.02 mmol) in dry dichloromethane (70 mL). The mixture was stirred at room temperature for 16 hours under a nitrogen atmosphere. Saturated aqueous NaHCO$_3$ (60 mL) was added and the mixture was extracted with dichloromethane (3×50 mL). The combined organic extract was dried (MgSO$_4$) and the solvent was evaporated under reduced pressure to give 10 (0.92 g, 65%) as a pale yellow oil: IR (KBr) ν 2936, 1708, 1059 cm$^{-1}$; $^1$H NMR (300 MHz; CDCl$_3$) δ 0.87 (9 H, t), 1.25 (18 H, m), 1.38 (6 H, m), 2.51 (6 H, t), 2.70 (6 H, t), 2.81 (6 H, t), 3.46 (6 H, t), 3.92 (6 H, t); $^{13}$C NMR (75 MHz; CDCl$_3$) δ 14.07, 22.68, 26.89, 27.43, 31.80, 40.72, 42.18, 51.20, 54.67, 56.28, 149.33.

Synthesis of 1 (R$^6$=n-hexyl). To freshly distilled N,N-dimethylformamide (600 mL) at 90° C. under nitrogen was added simultaneously a solution of 10 (0.545 g, 0.781 mmol) in N,N-dimethylformamide (50 mL) and a mixture of cyanuric acid (0.100 g, 0.775 mmol) and 1,8-diazabicyclo[5.4.0]undec-7-ene (0.70 mL, 0.71 g, 4.7 nmmol) in N,N-dimethylformamide (50 mL) via syringe pump over a 10 hour period. The resulting solution was further stirred for 16 hours at 90° C. The reaction was cooled to room temperature and the solvent was removed under reduced pressure. Purification of the residue by column chromatography on silica gel (2 to 7% MeOH: CH$_2$Cl$_2$) gave 1 (R$^6$=n-hexyl) (0.167 g, 30%) as a white solid: IR (KBr) 2924, 2358, 1691, 759 cm$^{-1}$; $^1$H NMR (300 MHz; CDCl$_3$) δ 0.83 (9 H, t), 1.31 (24 H, m), 2.85 (18 H, m), 3.95 (12 H, t); $^{13}$C NMR (75 MHz; CDCl$_3$) δ 14.34, 19.81, 22.97, 27.69, 32.28, 40.65, 46.36, 51.42, 149.47; MS m/z calcd for C$_{36}$H$_{64}$N$_9$O$_6$ 718.5 [M+1]$^+$, found 718.7.

Example 2

Preparation of Compound 1: R$^6$=Benzyl

Scheme 4 starts from the commercially available 1,3,5-tris (2-hydroxyethyl)cyanuric acid 11, which was converted to the tris-tosylate 12 and thereby to the tris-azide 13. Reduction of 13 provided the tris-amine 14, which was benzylated by reductive amination with benzaldehyde and sodium borohydride to give 15.

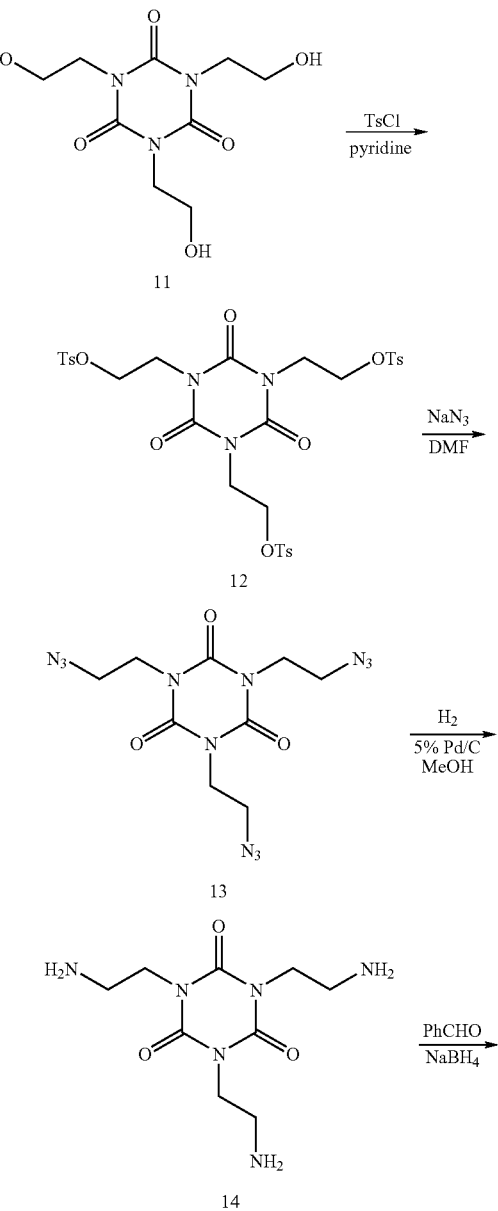

Scheme 4. Preparation of Compound 1 (R$^6$ = benzyl).

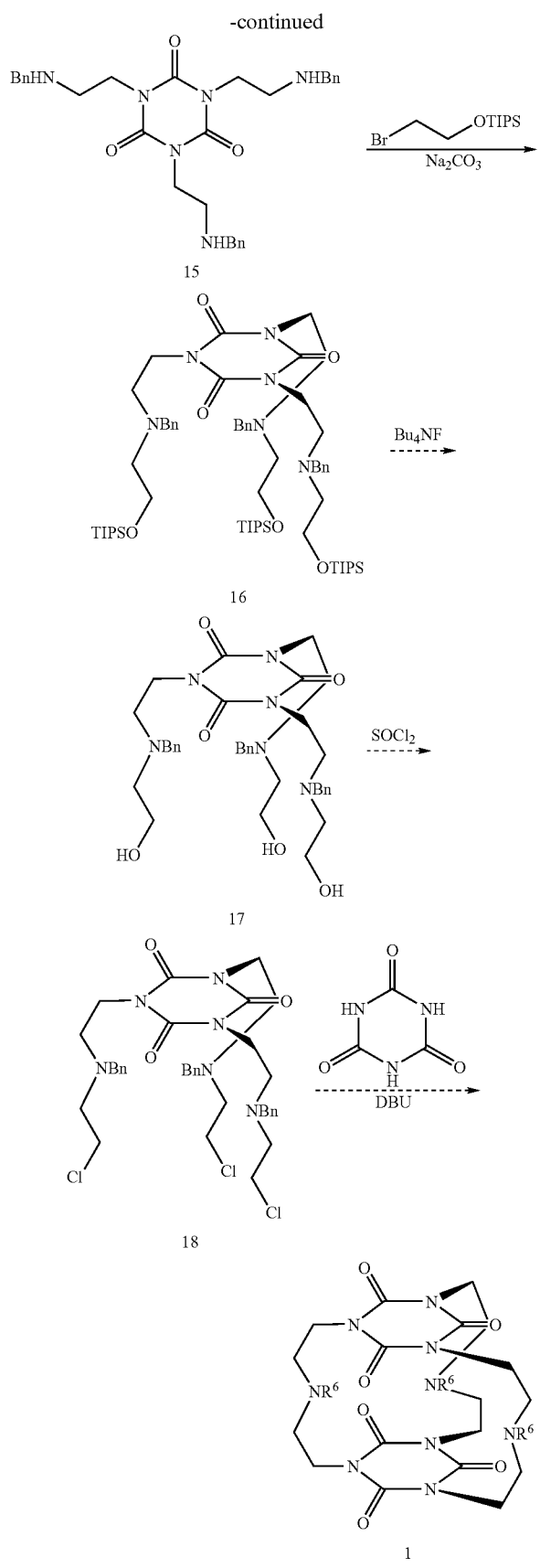

Synthesis of 12. A solution of p-toluenesulfonyl chloride (7.88 g, 41.3 mmol) in pyridine (10 mL) was cooled to −30° C. and 1,3,5-tris(2-hydroxyethyl)cyanuric acid 11 (3.00 g, 11.5 mmol) was added. The solution was stirred at −10° C. for 1 hour and then at 0° C. for 16 hours. The mixture was poured onto ice (100 g) and the resulting precipitate was collected, washed with water (400 mL), and dried in vacuum to give 12 (7.7 g, 97%) as white solid. 1H-NMR (CDCl3, 300 MHz) δ 2.42 (s, 3H), 4.13 (t, 2H), 4.25 (t, 2H), 7.24-7.38 (m, 2H), 7.66-7.81 (m, 2H); 13C-NMR (CDCl3, 75 MHz) δ 21.8, 41.8, 66.1, 128.1, 130.1, 132.8, 145.4, 148.6.

Synthesis of 13. To a solution of 12 (1.31 g, 1.90 mmol) in N,N-dimethylformamide (50 mL) was added sodium azide (880 mg, 13.5 mmol). The solution was stirred at 80° C. for 3 days. The solvent was removed under reduced pressure and the residue was partitioned between saturated aq. NaHCO3 (200 mL) and ether (400 mL). The organic layer was dried over Na2SO4, and the solvent evaporated to give 13 (440 mg, 69%) as white solid. 1H-NMR (CDCl3, 300 MHz) δ 3.57 (t, 1H), 4.60 (t, 1H); 13C-NMR (CDCl3, 75 MHz) δ 41.9, 48.6, 148.8.

Synthesis of 14. To a solution of triazide 13 (200 mg, 0.595 mmol) in MeOH (15 mL) was added 5% Pd/C (120 mg), and the mixture was stirred under an H2 atmosphere for 6 hours. The catalyst was filtered off and washed with additional MeOH (50 mL). The solvent was evaporated to give 14 (154 mg, 100%) as a white solid. 1H-NMR (CD3OD, 300 MHz) δ 2.98 (t, 2H), 4.02 (t, 2H); 13C-NMR (CD3OD, 75 MHz) 6 39.1, 44.0, 150.3.

Synthesis of 15. A solution of 14 (232 mg, 0.893 mmol) in ethanol (5 mL) was added to a stirred solution of benzaldehyde (300 mg, 2.83 mmol) in ethanol (5 mL). After 4 hours the mixture was cooled to 10° C. and sodium borohydride (202 mg, 5.34 mmol) was added. The reaction was then allowed to come to RT and stirred for 16 hours, after which it was diluted with water (50 mL), acidified with aq. 1 M HCl to pH 2, and extracted with CH2Cl2 (2×50 mL). The aq. layer was then adjusted to pH 10 with aq. 1 N NaOH, and extracted with CH2Cl2 (3×50 mL). The combined organic layer was washed with brine (50 mL), dried (Na2SO4), and the solvent evaporated. The residue was purified by column chromatography on silica gel (5:1 CH2Cl2:methanol) to give 15 (270 mg, 58%). 1H-NMR (CDCl3, 300 MHz) δ 2.90 (t, 2H), 3.76 (s, 2H), 4.05 (t, 2H), 7.18-7.38 (m, 5H); 13C-NMR (CDCl3, 75 MHz) δ 42.4, 46.6, 53.4, 127.2, 128.4, 128.6, 140.1, 149.8.

Preparation of 1 ($R^6$=benzyl). Alkylation of 15 with triisopropylsilyl O-protected 2-bromoethanol can provide the tris-2-TIPSO-ethylamino derivative 16 which can be deprotected with tetrabutylammonium fluoride (Bu4NF) to the tris-2-hydroxyethylamino derivative 17 using the procedure set forth for compound 9. Reaction of 17 with thionyl chloride can give the tris-2-chloroethylamino derivative 18 using the procedure set forth for compound 10. Compound 18, on reaction with the cyanuric acid in the presence of the base 1,8-diazabicyclo[5.4.0]undec-7-ene (DBU) using the procedure set forth for compound 1 ($R^6$=n-hexyl), can then provide the cyclophane compound 1 ($R^6$=benzyl).

Example 3

Preparation of Compound 3

Compound 3 can be prepared from 1 by attachment of linker L to a bridging nitrogen, forming an amide, 2. Reaction with biological molecule B under conditions sufficient to form an amide can provide 3. Amide formation can proceed through DCC coupling (*Journal of the Am. Chem. Soc.*, 1955, 77, 1067) or through acid halide coupling, among others.

Protonation of compound 3 and capture of fluoride-18 can be accomplished under acidic conditions (using an acid such as HCl, $HBF_4$, etc.) or neutral conditions, in the presence of a source of accelerator-produced $^{18}F$.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound having the formula:

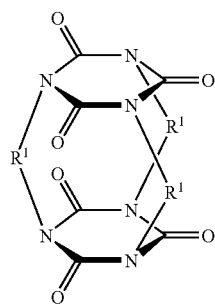

wherein
$R^1$ is

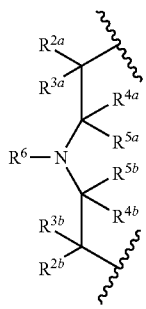

wherein
$R^{2a}$, $R^{2b}$, $R^{3a}$ and $R^{3b}$ are each hydrogen;
$R^{4a}$ and $R^{5a}$ and $R^{4b}$ and $R^{5b}$ are each hydrogen, or combined to form =O;
each $R^6$ is independently a member selected from the group consisting of H, optionally substituted $C_1$-$C_{10}$ alkyl, $C_1$-$C_6$ alkyl-$CO_2H$, $C_1$-$C_6$ alkyl-$CONHR^7$, optionally substituted $C_6$-$C_{12}$ aryl and L, wherein L is a linker selected from the group consisting of

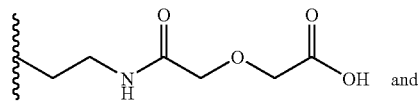

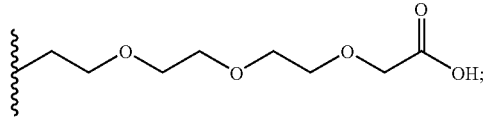

each $R^7$ is independently a member selected from the group consisting of H and $C_1$-$C_6$ alkyl;
or $R^{4a}$, $R^{5a}$ and $R^6$ or $R^{4b}$, $R^{5b}$ and $R^6$ are combined to form a 5-6 membered heteroaryl ring having from 1-3 heteroatoms each independently selected from the group consisting of N, O and S, optionally substituted with 1-3 $R^8$;
or $R^{2a}$, $R^{2b}$, $R^{3a}$, $R^{3b}$, $R^{4a}$, $R^{4b}$, $R^{5a}$, $R^{5b}$ and $R^6$ are combined to form a 11-14 membered heteroaryl ring having from 1-3 heteroatoms each independently selected from the group consisting of N, O and S, optionally substituted with 1-3 $R^8$;
each $R^8$ is independently a member selected from the group consisting of H, optionally substituted $C_1$-$C_6$ alkyl, optionally substituted $C_5$-$C_{10}$ cycloalkyl, optionally substituted $C_6$-$C_{12}$ aryl, optionally substituted $C_5$-$C_{12}$ heteroaryl and L;
wherein the substituted alkyl and substituted cycloalkyl groups are substituted with a member selected from the group consisting of —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$, wherein R', R" and R'" are each independently selected from the group consisting of hydrogen, unsubstituted ($C_1$-$C_8$)alkyl and heteroalkyl, unsubstituted aryl, unsubstituted alkyl, alkoxy or thioalkoxy groups, or aryl-($C_1$-$C_4$)alkyl groups;
wherein the substituted aryl and substituted heteroaryl groups are substituted with a member selected from the group consisting of -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, wherein R', R" and R'" are independently selected from the group consisting of hydrogen, ($C_1$-$C_8$) alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl;
and pharmaceutically acceptable salts and isomers thereof.

2. The compound of claim 1, wherein $R^1$ is a member selected from the group consisting of:

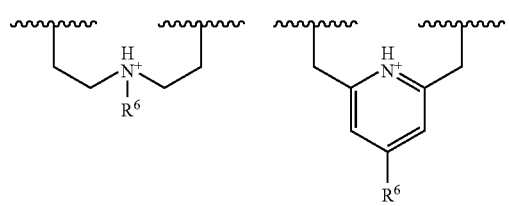

-continued

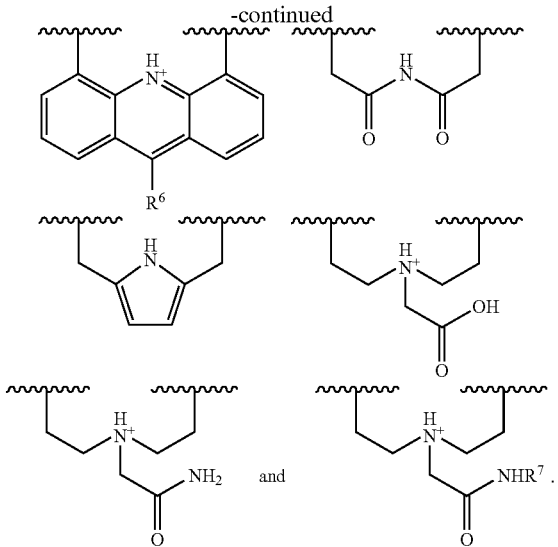

3. The compound of claim 2, wherein $R^1$ is:

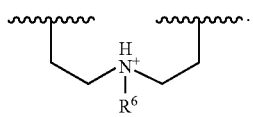

4. The compound of claim 1, wherein $R^{2a}$, $R^{2b}$, $R^{3a}$, $R^{3b}$, $R^{4a}$, $R^{4b}$, $R^{5a}$ and $R^{5b}$ are each H.

5. The compound of claim 1, wherein $R^6$ is a member selected from the group consisting of $C_1$-$C_{10}$ alkyl and $C_6$-$C_{12}$ aryl.

6. The compound of claim 5, wherein $R^6$ is a member selected from the group consisting of hexyl and benzyl.

7. The compound of claim 1, wherein $R^1$ is

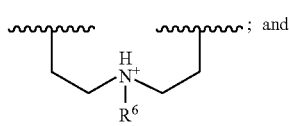

R6 is hexyl.

8. The compound of claim 1, wherein $R^1$ is

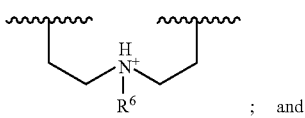

$R^6$ is benzyl.

9. A composition comprising a compound of claim 1 and a pharmaceutical excipient.

* * * * *